United States Patent
Kim et al.

(10) Patent No.: US 12,054,752 B2
(45) Date of Patent: Aug. 6, 2024

(54) HLA-A2 SUBTYPE-SPECIFIC PLK1-DERIVED EPITOPE INDUCING ANTIGEN-SPECIFIC T CELL IMMUNE RESPONSE TO PLK1 PROTEIN

(71) Applicant: THE CATHOLIC UNIVERSITY OF KOREA INDUSTRY-ACADEMIC COOPERATION FOUNDATION, Seoul (KR)

(72) Inventors: Tai Gyu Kim, Seoul (KR); Hyun Il Cho, Suwon-si (KR); Un Hee Kim, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 910 days.

(21) Appl. No.: 16/622,687

(22) PCT Filed: Jun. 12, 2018

(86) PCT No.: PCT/KR2018/006651
§ 371 (c)(1),
(2) Date: Dec. 13, 2019

(87) PCT Pub. No.: WO2018/230938
PCT Pub. Date: Dec. 20, 2018

(65) Prior Publication Data
US 2020/0115684 A1    Apr. 16, 2020

(30) Foreign Application Priority Data

Jun. 13, 2017   (KR) .................. 10-2017-0073893

(51) Int. Cl.
| | |
|---|---|
| *A61K 35/15* | (2015.01) |
| *A61K 35/17* | (2015.01) |
| *A61K 38/45* | (2006.01) |
| *C07K 14/74* | (2006.01) |
| *C12N 5/0783* | (2010.01) |
| *C12N 9/12* | (2006.01) |
| *A61K 38/00* | (2006.01) |

(52) U.S. Cl.
CPC ............... *C12N 9/12* (2013.01); *A61K 35/17* (2013.01); *A61K 38/45* (2013.01); *C07K 14/70539* (2013.01); *C12N 5/0638* (2013.01); *C12Y 207/11021* (2013.01); *A61K 35/15* (2013.01); *A61K 38/00* (2013.01); *C12N 2501/727* (2013.01)

(58) Field of Classification Search
CPC ......... A61K 35/17; A61K 38/00; A61K 35/15
See application file for complete search history.

(56) References Cited

U.S. PATENT DOCUMENTS

| 6,358,738 B1 * | 3/2002 | Erikson | A61K 38/45 |
| | | | 435/375 |
| 2006/0165711 A1 | 7/2006 | Bot et al. | |
| 2014/0105923 A1 | 4/2014 | Kim | |
| 2017/0037093 A1 | 2/2017 | Mahr et al. | |

FOREIGN PATENT DOCUMENTS

| KR | 10-2007-0094641 A | 9/2007 |
| KR | 10-2012-0119538 A | 10/2012 |

OTHER PUBLICATIONS

Park et al. (Cancer Sci. Aug. 2011; 102 (8): 1448-54).*
Clay et al. (Proc. Natl. Acad. Sci. USA. Jun. 1, 1993; 90 (11): 4882-6).*
Hassan et al. (J. Biol. Chem. Jan. 30, 2015; 290 (5): 2593-603).*
Ahmad (FASEB J. Jan. 2004; 18 (1): 5-7).*
Barouch et al. (J. Exp. Med. Dec. 1, 1995; 182 (6): 1847-56).*
International Search Report and Written Opinion issued by the International Searching Authority (ISA/KR) in PCT Application No. PCT/KR2018/006651 on Sep. 21, 2018. 12 pages, including English translation of International Search Report.
Li, Fan, et al. "Identification and modification of an HLA-A* 0201-restricted cytotoxic T lymphocyte epitope from Ran antigen." Cancer Immunology, Immunotherapy 58.12 (2009): 2039-2049.
Park, Jung-Sun, et al. "Induction of antitumor immunity using dendritic cells electroporated with Polo-like kinase 1 (Plk1) mRNA in murine tumor models." Cancer science 102.8 (2011): 1448-1454.

* cited by examiner

*Primary Examiner* — Stephen L Rawlings
(74) *Attorney, Agent, or Firm* — Meunier Carlin & Curfman LLC

(57) ABSTRACT

The present invention relates to a HLA-A2 subtype-specific PLK1-derived epitope inducing an antigen-specific T cell immune response to a PLK1 protein. More specifically, a HLA-A2 subtype-specific PLK-1-derived epitope inducing an antigen-specific T cell immune response to a PLK1 protein according to the present invention can provide a CD8+ T cell immune response specific for tumor cells.

7 Claims, 7 Drawing Sheets
Specification includes a Sequence Listing.

HLA-A2 SUBTYPE-SPECIFIC PLK1-DERIVED EPITOPE INDUCING ANTIGEN-SPECIFIC T CELL IMMUNE RESPONSE TO PLK1 PROTEIN

CROSS REFERENCE TO RELATED APPLICATIONS

This application is a national stage application filed under 35 U.S.C. § 371 of PCT/KR2018/006651, filed Jun. 12, 2018, which claims the benefit of Korean Patent Application No. 10-2017-0073893, filed on Jun. 13, 2017, applications which are incorporated herein by reference in their entirety.

BACKGROUND

1. Field of the Invention

The present invention relates to a HLA-A*0201 subtype-specific PLK1-derived epitope inducing an antigen-specific T cell immune response to a PLK1 protein.

2. Discussion of Related Art

A T cell immune response to all antigens starts while T cells are activated by recognizing an MHC/peptide antigen complex presented on the surface of an antigen presenting cell (APC) after an antigen-derived peptide fragment (epitope) and a major histocompatibility complex (MHC) are bound to each other by an antigen processing process of the antigen presenting cell (APC).

T cells specifically responding to an antigen activate another immune response by secreting various cytokines, or are differentiated into killer T cells having a cytotoxic function which recognizes and kills target cells presenting a MHC/peptide antigen complex.

A minimum antigen-derived peptide fragment inducing such a T cell immune response is called an epitope, and the degree of T cell activation varies depending on the binding affinity between the epitope and the MHC molecule. It has been reported that the MHC molecule has various subtypes in each person, MHC molecules may have various binding affinities for a single epitope, and specific peptides may bind to various different MHC subtypes to be presented on the surface of cells.

Since the antigen recognition by CD8+T cells differentiated into killer T cells having a cytotoxic function is regulated by various allele subtypes of the MHC class-I gene, the investigation of an epitope responding to the MHC class-I subtype present in a number of humans should be essentially conducted for the identification of a candidate material for use in the development of tumor vaccines or T-cell immunotherapies inducing highly efficient anti-tumor immune responses. The MHC molecule expressed in humans is a human leukocyte antigen (HLA), the most commonly expressed/existing human leukocyte antigen (HLA) subtype is a HLA-A2 subtype, and among the HLA-A2 subtypes, studies on HLA-A*0201 have been most actively conducted.

The Polo-like kinase-1 (PLK1) is an essential mitotic kinase regulating various cell division processes, and has been reported to be expressed at a level higher than a normal tissue in a solid cancer including lung cancer, breast cancer, thyroid cancer, colorectal cancer, prostate cancer, ovarian cancer, and the like, and since it was revealed that the death of tumor cells may be induced by suppressing the phosphorylation of a target-protein by the PLK1 protein, PLK1 inhibitors as anticancer drugs have been in a stage of universalization through Clinical I, II, and III phases. In addition, it has been reported that the PLK1 protein is overexpressed in tumor cells, and thus may be used as a tumor-target antigen inducing a tumor-specific T cell immune response.

However, the epitope of PLK1 specific for HLA-A2 inducing an antigen-specific T cell immune response specific for the PLK1 protein has not been reported yet.

SUMMARY OF THE INVENTION

An object of the present invention is to provide a PLK1-derived epitope specific for HLA-A2 subtypes inducing an antigen-specific T cell immune response to a PLK protein.

Another object of the present invention is to provide a pharmaceutical use of the PLK1-derived epitope.

To achieve the objects, the present invention provides an epitope of polo-like kinase 1 (PLK1), which is selected from the group consisting of SEQ ID NOS: 1 to 4, specific for HLA-A2 subtypes, and recognized by a cytotoxic T lymphocyte (CTL).

The present invention also provides a composition for preventing or treating tumors, the composition including: an epitope of polo-like kinase 1 which is recognized by a cytotoxic T lymphocyte.

Further, the present invention provides a method for treating tumors, the method including: administering an effective amount of a composition for preventing or treating tumors, including an epitope of polo-like kinase 1 which is recognized by a cytotoxic T lymphocyte, to a subject in need thereof.

The present invention also provides an antigen presenting cell, wherein the antigen presenting cell presents a complex of the epitope of polo-like kinase 1 recognized by the cytotoxic T lymphocyte and a MHC class I antigen or II antigen on its surface.

The present invention also provides a composition for preventing or treating tumors, the composition including the antigen presenting cell.

In addition, the present invention provides a method for treating tumors, the method including: administering an effective amount of the composition for preventing or treating tumors, the composition including the antigen presenting cell, to a subject in need thereof.

The present invention also provides a cytotoxic T lymphocyte, wherein the cytotoxic T lymphocyte specifically recognizes the complex of the epitope of polo-like kinase 1 and the MHC class I antigen or II antigen, and wherein the complex is presented on the antigen presenting cell.

The present invention also provides a composition for preventing or treating tumors, including the cytotoxic T lymphocyte.

Furthermore, the present invention provides a method for treating tumors, the method including: administering an effective amount of the composition for preventing or treating tumors, the composition including the cytotoxic T lymphocyte, to a subject in need thereof.

The present invention has an effect of providing a PLK-1-derived epitope specific for a HLA-A2 subtype inducing an antigen-specific T cell immune response to a PLK1 protein. The PLK1-derived epitope can be used for prevention or treatment of a cancer specifically expressing PLK1.

DETAILED DESCRIPTION OF EXEMPLARY EMBODIMENTS

Figure 1:
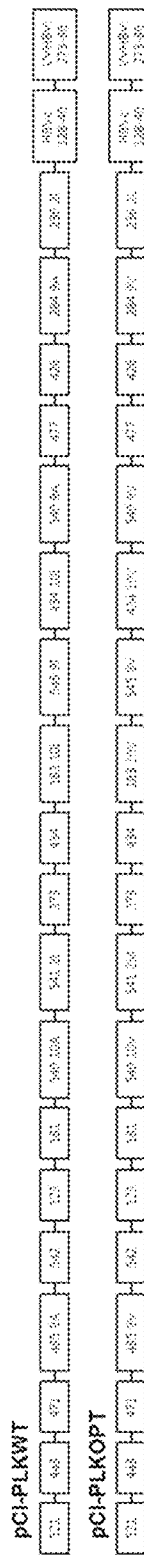
FIG. 1 illustrates a PK1 sequence having wild-type epitope sequences (top, SEQ ID NO: 5) optimized for recombination, and an expression vector (bottom, SEQ ID NO: 6) into which a recombinant DNA including multiple epitopes of PLK1 is inserted.

The present inventors investigated a PLK1-derived epitope specific for a HLA-A*0201 subtype inducing an antigen-specific T cell immune response to a PLK1 protein using transgenic mice expressing a HLA-A2 major histocompatibility complex, and confirmed that the induced CD8+T cells could specifically recognize HLA-A2-positive tumors using the investigated PLK-1-derived epitope, thereby completing the present invention.

Accordingly, the present invention provides polo-like kinase 1 (PLK1), which is selected from the group consisting of SEQ ID NOS: 1 to 4, specific for HLA-A2 subtypes, and recognized by a cytotoxic T lymphocyte (CTL).

As used herein, the term "epitope" refers to a peptide epitope of CTL inducing an immune response of CD8+T cells in an individual expressing a HLA-A2 subtype. The present inventors selected and recommended 28 peptides of PLK1 expected to have high binding affinity for HLA-A*0201 using a bioinformatics program in human or mouse PLK1. The 28 epitope peptides include about 9 and 10 amino acids, respectively. The binding affinity refers to "a degree to which the epitope binds to a major histocompatibility complex on the surface of an antigen presenting cell", and it is known that the higher the binding affinity is, the more efficient the activation of T cells is.

As used herein, the term "major histocompatibility complex (MHC)" is a site having a high level of polymorphism inducing T cell differentiation by binding to a T cell receptor along with a foreign antigen when the antigen presenting cell presents the foreign antigen, and is an important cellular surface molecule determining histocompatibility during organ transplantation. The MHC class I immune response refers to a response carried out by CD8+T cells stimulated by an epitope presented by the antigen presenting cell going through the MHC class I pathway in an immune response to a tumor antigen, and CD8+T cells carry out two functions of IFN-γ secretion and cytotoxicity.

As used herein, the term "human leukocyte antigen (HLA)" is a human MHC, and is expressed on the surface of human leukocytes. The HLA-A2 supertype is one of the most frequent HLAs, is expressed in an amount of 40 to 50% in Asian and Western people, and includes a subtype such as A*0201, A*0202, A*0203, A*0204, A*0205, A*0206, A*0207, A*6802, and A*6901. In the present invention, an epitope peptide of the PLK1 responding to the MHC present in a HLA-A2 subtype human was selected.

Accordingly, the epitope of PLK1 of the present invention is a peptide specific for the HLA-A2 subtype recognized by CTL, more specifically, the HLA-A*0201 subtype, and may be an amino acid sequence described in SEQ ID NOS: 1($PLK1_{123}$), 2($PLK1_{477}$), 3($PLK1_{541\ 21}$), and 4($PLK1_{542}$) derived from mice or humans.

The present invention also provides a composition for preventing or treating tumors, the composition including the epitope of polo-like kinase 1 which is recognized by the cytotoxic T lymphocyte.

A medicament containing the epitope of PLK1 of the present invention as an active ingredient may prevent tumors, suppress the relapse of tumors, or treat tumors, for example, by administering, to a patient with a tumor, and the like, the epitope of PLK1 of the present invention alone or using a cell carrier. The epitope of PLK1 of the present invention binds to the MHC class I antigen or II antigen on an antigen presenting cell to be presented at high density on the surface of cells, and thus, the tumor-specific CTL is efficiently proliferated in vivo, thereby preventing tumors, suppressing the relapse of tumors, and treating tumors.

The tumor overexpresses PLK1, and examples thereof include malignant melanoma, lymphoma, colon cancer, neuroglioma, renal cancer, ovarian cancer, breast cancer, glioblastoma, leukemia, and cervical cancer, but are not limited thereto.

The composition of the present invention may be administered with an immune-enhancing agent (or adjuvant) or as a particulate formulation such that cellular immunity may be effectively established together with the epitope of PLK1.

The adjuvant is a material that non-specifically enhances an immune response to an antigen during the initial activation of immune cells, and refers to a preparation, a molecule, and the like that are not immunogenic to a host, but strengthen immunity by enhancing the activity of cells of the immune system (Warren et al., *Annu Rev Immunol* 4: 369, 1986). The adjuvant which may be administered with the composition of the present invention to enhance the immune response includes various adjuvants, and as a typical adjuvant, a Freund's adjuvant, an alum compound, a muramyl dipeptide, a lipopolysaccharide (LPS), monophosphoryl lipid A, Quil A, or the like is known. The adjuvant may be administered simultaneously with a composition for preventing tumors (vaccine) or may be administered sequentially at time intervals.

Further, the present invention provides a method for treating tumors, the method including: administering an effective amount of a composition for preventing or treating tumors, the composition including an epitope of polo-like kinase 1 which is recognized by a cytotoxic T lymphocyte, to a subject in need thereof.

The subject may be a mammal such as a dog, a cat, a rat, a mouse, and a human, but is not limited thereto.

The present invention also relates to an antigen presenting cell in which a complex of the epitope of polo-like kinase 1 recognized by the cytotoxic T lymphocyte and a MHC class I antigen or II antigen is presented on its surface.

The antigen presenting cell may be any one or more selected from the group consisting of a dendritic cell, a mononuclear cell, a CD4+T cell, a B cell, and a gamma delta T (γδ T) cell, and the CD4+T cell, the B cell, and the γδT cell are preferably in a naive state, an activated state, or an expanded state, but are not limited thereto.

The antigen presenting cell may be prepared by introducing a nucleic acid encoding the epitope of PLK1 recognized by CTL into the antigen presenting cell.

The nucleic acid is used in the broadest sense, and includes a single-stranded (ss) DNA, a double-stranded (ds) DNA, a cDNA, a (−)-RNA, a (+)-RNA, a dsRNA, and the like.

As the method for introducing the nucleic acid of the present invention into the antigen presenting cell, a method by a vector may be used, but the method is not limited thereto.

As used herein, the term "vector" refers to a nucleic acid molecule capable of transporting another nucleic acid to which it has been linked. One type of vector is a "plasmid", which refers to a circular double-stranded DNA loop into which additional DNA segments can be ligated. Another type of vector is a viral vector, in which additional DNA segments can be ligated into the viral genome. Certain vectors are capable of autonomous replication in a host cell upon introduction into the host cell (for example, bacterial vectors having a bacterial origin of replication and episomal mammalian vectors). Other vectors (for example, non-episomal mammalian vectors) are integrated into the genome of a host cell upon introduction into the host cell, and thereby may be replicated along with the host genome. Moreover, certain vectors are capable of directing the expression of genes to which they are operably linked. As used herein, such vector refers to a "recombinant expression vector" (or simply, "expression vector"). In general, expression vectors useful in recombinant DNA techniques are predominantly in the form of plasmids, and "plasmid" and "vector" may be used interchangeably as the plasmid is a type of vector most commonly used. However, the present invention also includes other types of expression vectors such as viral vectors providing an equivalent function (for example, an adenoviral vector, an adeno-associated viral (AAV) vector, a herpes viral vector, a retroviral vector, a lentiviral vector, and a baculoviral vector). Preferably, a lentiviral vector may be used. Transformation includes any method of introducing nucleic acids into organisms, cells, tissues or organs and may be performed by selecting a suitable standard technology depending on the type of host cell as known in the art. Examples of this method include electroporation, protoplast fusion, calcium phosphate ($CaPO_4$) precipitation, calcium chloride ($CaCl_2$) precipitation, agitation using silicon carbide fiber, agrobacterium-mediated transformation, PEG, dextran sulfate, Lipofectamine, and the like, but are not limited thereto.

The present invention also relates to a composition for preventing or treating tumors, the composition including the antigen presenting cell.

In addition, the present invention provides a method for treating tumors, the method including: administering an effective amount of the composition for preventing or treating tumors, the composition including the antigen presenting cell, to a subject in need thereof.

The antigen presenting cell may be used as a vaccine or immunotherapeutic agent.

The vaccine (or immunogenic composition) refers to a material inducing anticancer immunity or tumor suppression when inoculated into an animal, the epitope of PLK1 of the present invention may induce a strong and specific immune response against cancer cells expressing PLK1, and examples of a cancer expressing PLK1 include malignant melanoma, lymphoma, colon cancer, neuroglioma, renal cancer, ovarian cancer, breast cancer, glioblastoma, leukemia, cervical cancer, and the like, but are not limited thereto.

The immunotherapeutic agent may increase an immune response or selectively boost a portion of the immune response preferred for treatment or prevention of tumors. When the antigen presenting cell of the present invention is introduced into cells to express an epitope of PLK1, the epitope of PLK1 binds to the MHC class I antigen or II antigen in the antigen presenting cell to be presented at high density on the cell surface, and thus, the tumor-specific CTL is efficiently proliferated in vivo, thereby preventing tumors, suppressing the relapse of tumors, and treating tumors.

The present invention also relates to a cytotoxic T lymphocyte specifically recognizing a complex of the epitope of polo-like kinase 1 recognized by the cytotoxic T lymphocyte and the MHC class I antigen or II antigen, and wherein the complex is presented on the antigen presenting cell.

The CTL preferably includes a CD4+T cell or a CD8+T cell that specifically recognizes a complex of epitope of PLK1/MHC class I antigen or II antigen presented to antigen presenting cells, but is not limited thereto.

The CTL is induced in vitro, and is included by bringing the CTL in vitro into contact with human type I or II MHC molecules loaded with the epitope of PLK1 expressed on the surface of suitable antigen presenting cells for a time sufficient to activate the CTL in an antigen-specific manner. Furthermore, it is possible to use methods for producing CTL using autologous-tumor-infiltrating lymphocytes; preparing CTL using autologous peripheral blood lymphocytes; producing autologous CTL by pulsing the epitope of PLK1 into dendritic cells and using the dendritic cells, or using a recombinant virus to infect cells; using macrophages pulsed with the epitope of PLK1 or infected by the recombinant virus for the preparation of autologous CTL; or preparing CTL though sensitization of T cells in vitro using an artificial presenting cell, but the method is not limited thereto.

The induction of CTL may be evaluated by presenting the epitope of PLK1 to T cells by the antigen presenting cell to detect the induction of CTL. Further, the antigen presenting cell has an effect of activating CD4+T cells, CD8+T cells, macrophages, eosinophils, and NK cells. Since CD4+T cells are also important for anticancer immunity, the anticancer immune inducing action of the epitope of PLK1 may be evaluated using the activation effects of the aforementioned cells as an index.

The present invention also relates to a composition for preventing or treating tumors, the composition including the cytotoxic T lymphocyte.

Further, the present invention provides a method for treating tumors, the method including: administering an effective amount of the composition for preventing or treating tumors, the composition including the cytotoxic T lymphocyte to a subject.

The CTL activated by the epitope of PLK1 is useful for treatment of tumors.

The activated CTL will selectively recognize cells abnormally expressing PLK1. Preferably, the CTL recognizes cells through interaction (for example, binding) with a HLA/peptide complex through TCR. In patients, the CTL is useful for a method for killing a target cell abnormally expressing PLK1. An effective amount of activated CTL is administered to patients. The CTL administered to patients may be derived or activated from patients (that is, this is autologous CTL). Furthermore, the CTL is derived from individuals other than the patient. Of course, preferably, a donor is a healthy individual. Here, the "healthy individual" means that the individual has a generally good health status, preferably has a competent immune system, and more preferably, does not have any disease readily tested or detected.

Here, the "abnormally expressed" means that the expression of PLK1 is overexpressed as compared to the normal level, or the gene is silent in a tissue from which the tumor is derived, but is expressed in the tumor. The "overexpression" means that the PLK1 is present at 1.2-fold or more than the level present in normal tissues, and that the PLK is present at more preferably at least 2-fold, and even more preferably at least 5-fold or 10-fold in normal tissues.

In vivo, the target cell for the CTL of the present invention is a cell of a tumor (frequently expressing MHC type II) and/or a stromal cell surrounding a tumor (tumor cell)(also frequently expressing the MHC type II).

Accordingly, the CTL of the present invention may be an active ingredient in the therapeutic composition.

As a method for adopting and delivering CTL, a publicly-known method may be used, but is not particularly limited.

The composition for preventing or treating tumors of the present invention may include an active ingredient constituting a composition suitable for diagnostic or therapeutic use in vitro, in vivo, or ex vivo, and an active or inactive pharmaceutically active carrier.

The pharmaceutically acceptable carrier includes any pharmaceutical carrier compatible with T cells, such as a phosphate buffered saline solution and a protein excipient including serum albumin such as human serum albumin (HSA), recombinant human albumin (rHA), gelatin, casein, and the like.

As an example of carriers, stabilizers and adjuvants, Martin REMINGTON'S PHARM. SCI, 18th Ed. (Mack Publ. Co., Easton (1995)) and the "PHYSICIAN'S DESK REFERENCE", 58nd Ed., Medical Economics, Montvale, N.J. (2004) are referenced. The term "carrier" may include a buffer or a pH adjusting agent, and typically, the buffer is a salt prepared from an organic acid or base. A representative buffer includes organic acid salts such as salts of citric acid, salts of ascorbic acid, salts of gluconic acid, salts of carbonic acid, salts of tartaric acid, salts of succinic acid, salts of acetic acid, or salts of phthalic acid; Tris, tromethamine hydrochloride, or phosphate buffers. An additional carrier includes a polymeric excipient/additive such as polyvinylpyrrolidone, Ficoll® (a polymeric sugar), dextrate (for example, cyclodextrin, for example, 2-hydroxypropyl-quadrature,-cyclodextrin), polyethylene glycol, an antioxidant, an antistatic agent, a surfactant (for example, a polysorbate such as "TWEEN 20" and "TWEEN 80"), a lipid (for example, phospholipid, fatty acid), a steroid (for example, cholesterol), and a chelating agent (for example, EDTA). Agents for preventing or inhibiting freezing may also be included.

The composition for preventing or treating tumors of the present invention may be prepared in various formulations as appropriate. For example, formulations and carriers suitable for parenteral administration, such as by intratumoral, intraarterial (in the joints), intravenous, intramuscular, intradermal, intraperitoneal, intranodal and subcutaneous routes, include an antioxidant, a buffer, a bacteriostat, and a solute that renders the formulation isotonic with the blood of an intended recipient, and an aqueous and non-aqueous sterile suspension that may include a suspending agent, a solubilizer, a thickening agent, a stabilizer, and a preservative.

The intravenous or intraperitoneal administration is a method preferred for the administration of the composition for preventing or treating tumors of the present invention. The dose of cells administered to an individual is an amount effective to achieve a desired beneficial therapeutic response in the individual over time, or to inhibit growth of cancer cells, or to inhibit infection. For example, the administration may be performed by a method of obtaining and storing a blood sample from an individual prior to injected and by using the blood samples for subsequent analysis and comparison. In general, at least about $1 \times 10^4$ to $1 \times 10^6$ and typically, $1 \times 10^8$ to $1 \times 10^{10}$ cells may be injected intravenously or intraperitoneally into a 70 kg patient over roughly 60 to 120 minutes. For administration, cells of the present invention are administered at a rate determined by the LD-50 (or other methods of measuring toxicity) according to the cell type and the side-effects according to the cell type at various concentrations, in consideration of the overall health status and body weight of the individual. Administration may be accomplished via single or divided doses. The composition for preventing or treating tumors of the present invention may supplement other treatments for a specific symptoms using a known conventional therapeutic method including a cytotoxic agent, a nucleotide analog and a biologic response modifier. Similarly, the biological response modifier may be optionally added to treatment by the composition for preventing or treating tumors of the present invention.

Hereinafter, the present invention will be described in detail through the Examples. However, the following Examples are only for exemplifying the present invention, and the content of the present invention is not limited by the following Examples.

<Example 1> Selection of HLA-A*0201 Subtype-Specific PLK1-Derived Epitope Inducing Antigen-Specific T Cell Immune Response to PLK1 Protein PLK1-derived HLA-A2 subtype-specific epitope peptides were predicted using a bioinformatics-based program (Immune epitope database & analysis resource, http://www.iedb.orf), and 28 peptides were synthesized as shown in the following Table 1.

TABLE 1

| Peptide | Start | End | Length | WT (SEQ ID NO: 5) | OPT (SEQ ID NO: 6) |
|---|---|---|---|---|---|
| HLA-A*02:01 | 123 | 132 | 10 | SDFVFVVLEL | |
| (hPLK1) | 181 | 190 | 10 | NLFLNEDLEV | |
| | 183 | 192 | 10 | FLNEDLEVKI | FLNEDLEVKV |
| | 236 | 244 | 9 | SIGCIMYTL | SLGCIMYTL |
| | 284 | 292 | 9 | KMLQTDPTA | KMLQTDPTV |
| | 373 | 381 | 9 | HLSDMLQQL | |
| | 426 | 434 | 9 | QLCDNSVGV | |
| | 434 | 442 | 9 | VLFNDSTRL | |
| | 434 | 443 | 10 | VLFNDSTRLI | VLFNDSTRLV |
| | 443 | 451 | 9 | ILYNDGDSL | |
| | 471 | 479 | 9 | SLMKKITLL | |
| | 477 | 486 | 10 | TLLKYFRNYM | |
| | 485 | 493 | 9 | YMSEHLLKA | YMSEHLLKV |
| | 521 | 530 | 10 | IILHLSNGSV | |
| | 540 | 549 | 10 | KLILCPLMAA | KLILCPLMAV |
| | 540 | 548 | 9 | KLILCPLMA | KLILCPLMV |
| | 541 | 550 | 10 | LILCPLMAAV | LMLCPLMAAV |
| | 542 | 550 | 9 | ILCPLMAAV | |
| | 545 | 553 | 9 | PLMAAVTYI | PLMAAVTYV |

In order to use a DNA-based vaccination strategy inducing multi-epitope-specific T cell immune responses, an amino acid sequence of the predicted PLK1-derived HLA-A2 multi-epitope was linked to a furin-sensitive linker (SGSG) amino acid sensitive to a proteolytic enzyme of the Golgi apparatus and cloned into a pCI expression vector (see FIG. 1).

Recombinant DNA, PLKWT and PLKOPT were transfected into HLA-A2 transgenic mice and biological electric shock therapy was performed at 95 V (4×65 ms pulses with repoling) using an Electro square wave electroporation device (ECM830; BTX; San Diego, CA). After the biological electric shock therapy was performed 3 times at 7-day intervals, CD8+T cells of mouse spleens were isolated. IFN-γ EliSpot was performed by sensitizing T2 cell lines expressing HLA-A2 molecules with each predicted epitope peptide and using T2 cell lines as a target cell.

Figure 2A:
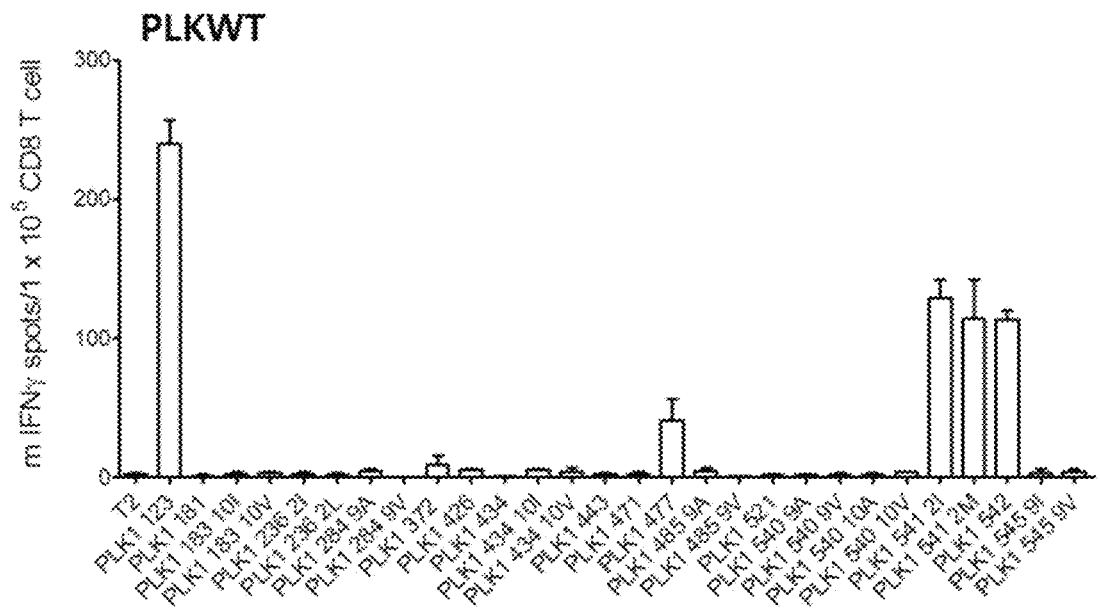
FIGS. 2A and 2B illustrate the EliSpot results confirming immune responses occurring in the spleen after HLA-A2 transgenic mice are subjected to electroporation with a recombinant DNA (FIG. 2A) including multiple wild-type PLK1 epitopes and a recombinant DNA (FIG. 2B) including multiple PLK1 epitopes optimized for recombination.
Figure 2A:
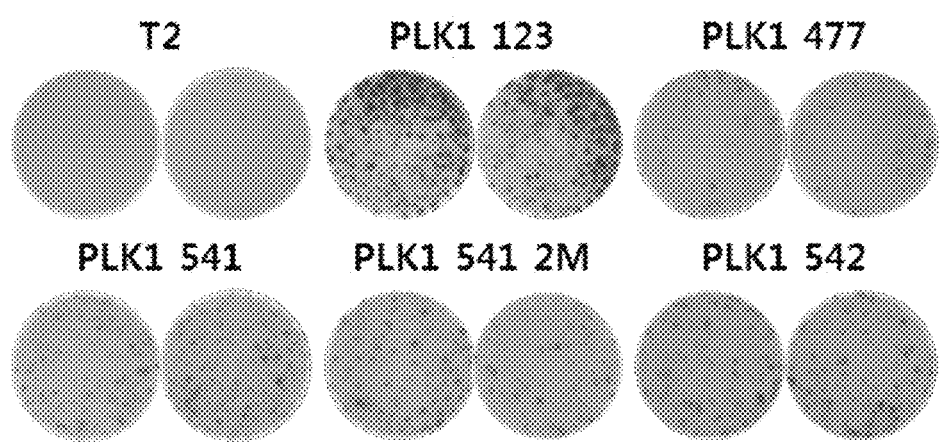
Figure 2B:
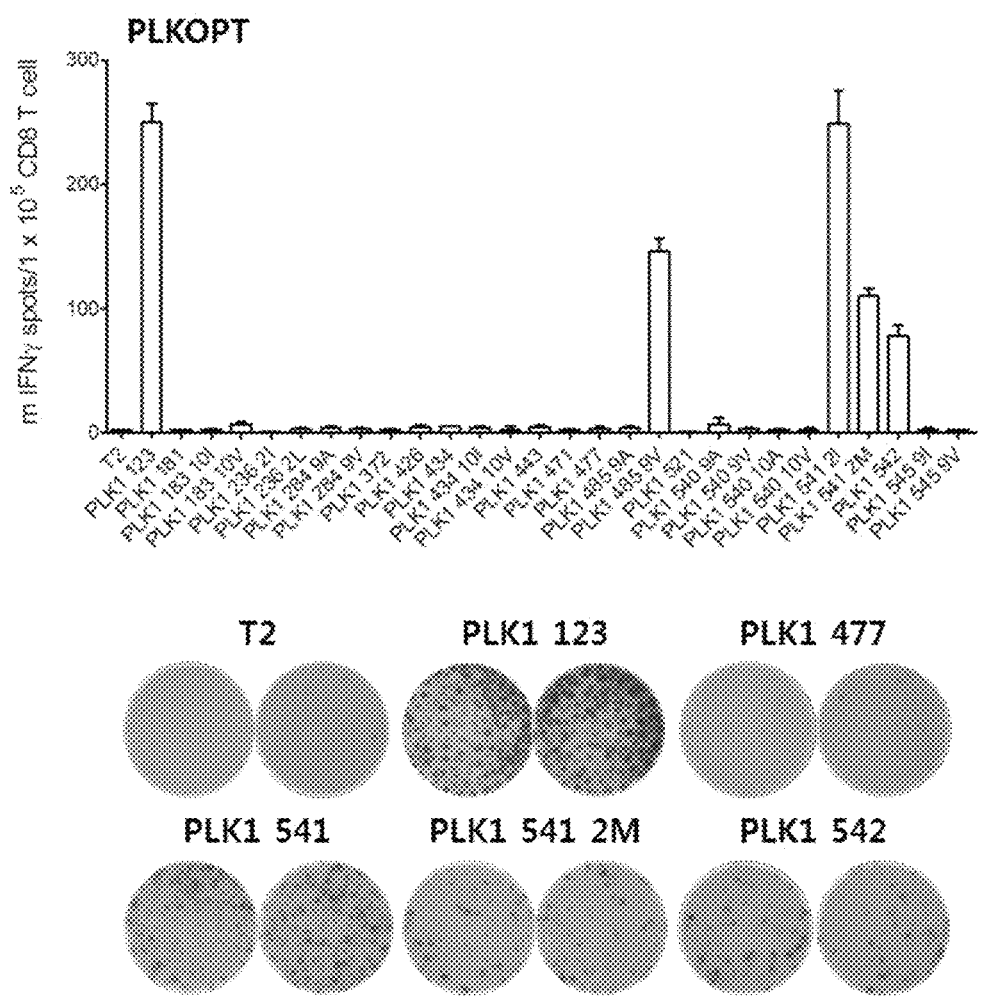

As illustrated in FIGS. 2A and 2B, it was observed that the ability to produce IFN-γ by the activation of CD8+T cells for T2 cell lines sensitized with each epitope peptide was exhibited at high levels when T2 cells were sensitized with PLK1-derived $PLK1_{123}$ (SDFVFVVLEL, SEQ ID NO: 1), $PLK1_{477}$ (TLLKYFRNYM, SEQ ID NO: 2), $PLK1_{541\ 21}$ (LILCPLMAAV, SEQ ID NO: 3), and $PLK1_{542}$ (ILCPLMAAV, SEQ ID NO: 4) peptides.

It was confirmed that the peptides of the sequences were HLA-A2-specific dominant epitopes.

Next, HLA-A2-binding $PLK1_{123}$ (SDFVFVVLEL, SEQ ID NO: 1), $PLK1_{477}$ (TLLKYFRNYM, SEQ ID NO: 2), and $PLK1_{541}$ (LILCPLMAAV, SEQ ID NO: 3) peptides confirmed as dominant epitopes were selected in a multi-epitope DNA-based vaccination experiment in the HLA-A2 transgenic mice, and immunized into the HLA-As transgenic mice by a dendritic cell vaccination and peptide-based TriVax vaccination (CD40 antibody/Poly-IC/epitope) strategy. After an immune response to each epitope-peptide was induced through this, T cells of the spleens were obtained and each cultured with a PLK1 antigen, and then CD8+T cells expressing IFN-γ and CD107a/b were confirmed using flow cytometry.

Figure 3:
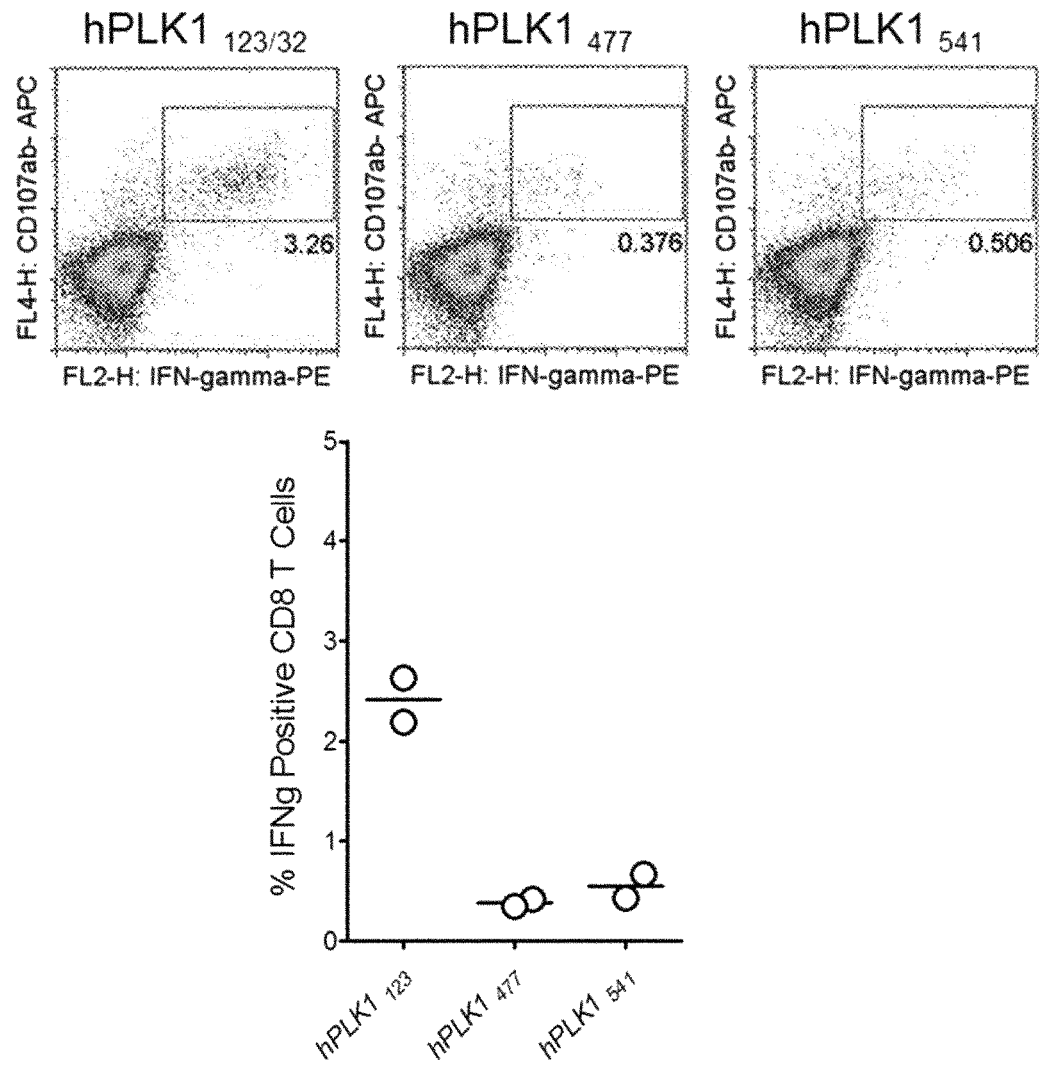
FIG. 3 illustrates flow cytometry analysis results confirming CD8+T cell immune responses of $PLK1_{123}$ (SDFVFVVLEL, SEQ ID NO: 1), $PLK1_{477}$ (TLLKYFRNYM, SEQ ID NO: 2), and $PLK1_{541/21}$ (LILCPLMAAV, SEQ ID NO: 3) among PLK-1-derived epitope candidates specific for HLA-A2 with CD107a/b.

As illustrated in FIG. 3, a relatively high rate of antigen-specific CD8+T cells was observed in a HLA-A2 transgenic mouse experimental group immunized with $PLK1_{123}$ antigen-peptide compared to an experimental group using $PLK1_{477}$ and $PLK1_{541}$ antigen-peptides.

In order to examine CD8+T cell immune responses, an immune response occurring in the spleen was confirmed by immunization into HLA-A2 transgenic mice by a dendritic cell vaccination and peptide-based vaccination strategy. For this purpose, HLA-A2-binding $PLK1_{123}$ (SNDFVFVVLEL, SEQ ID NO: 1), $PLK1_{477}$ (TLLKYFRNYM, SEQ ID NO: 2), and $PLK1_{541}$ (LILCPLMAAV, SEQ ID NO: 3) peptides confirmed as dominant epitopes were selected in a multi-epitope DNA-based vaccination experiment in the HLA-A2 transgenic mice, and immunized into the HLA-As transgenic mice by a dendritic cell vaccination and peptide-based TriVax vaccination (CD40 antibody/Poly-IC/epitope) strategy. After an immune response to each epitope-peptide was induced through this, CD8+T cells were obtained by antibody-binding magnetic cell sorting, and used as effector cells for confirming an antigen-specific T cell response. As a target cell, CCRF-SB, THP-1, and SKM-1 as HLA-A2-positive leukemia & lymphoma cells, and SK-MEL-5 as a melanoma cell were used. Further, the antigen-specific IFN-γ secretion of CD8+T cells was also confirmed through EliSpot by utilizing HL-60 (leukemia) and SK-MEL-3 (melanoma) as HLA-A2 negative cells.

Figure 4A:
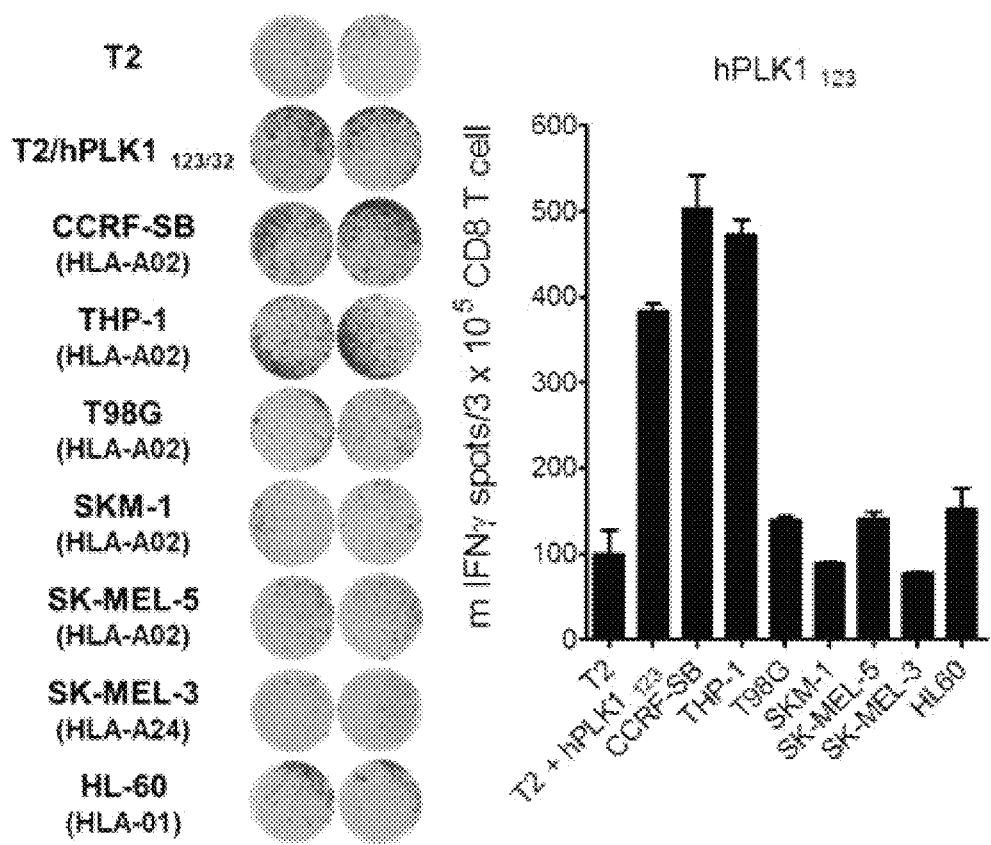
FIG. 4A to 4C illustrate the EliSpot results confirming immune responses occurring by immunization of HLA-A2 transgenic mice with $PLK1_{123}$ (SDFVFVVLEL, SEQ ID NO: 1)(FIG. 4A), $PLK1_{477}$ (TLLKYFRNYM, SEQ ID NO: 2)(FIG. 4B), and $PLK1_{541/21}$ (LILCPLMAAV, SEQ ID NO: 3)(FIG. 4C) among PLK1-derived epitope candidates specific for HLA-2 by a dendritic cell vaccination and peptide-based vaccination strategy.
Figure 4B:
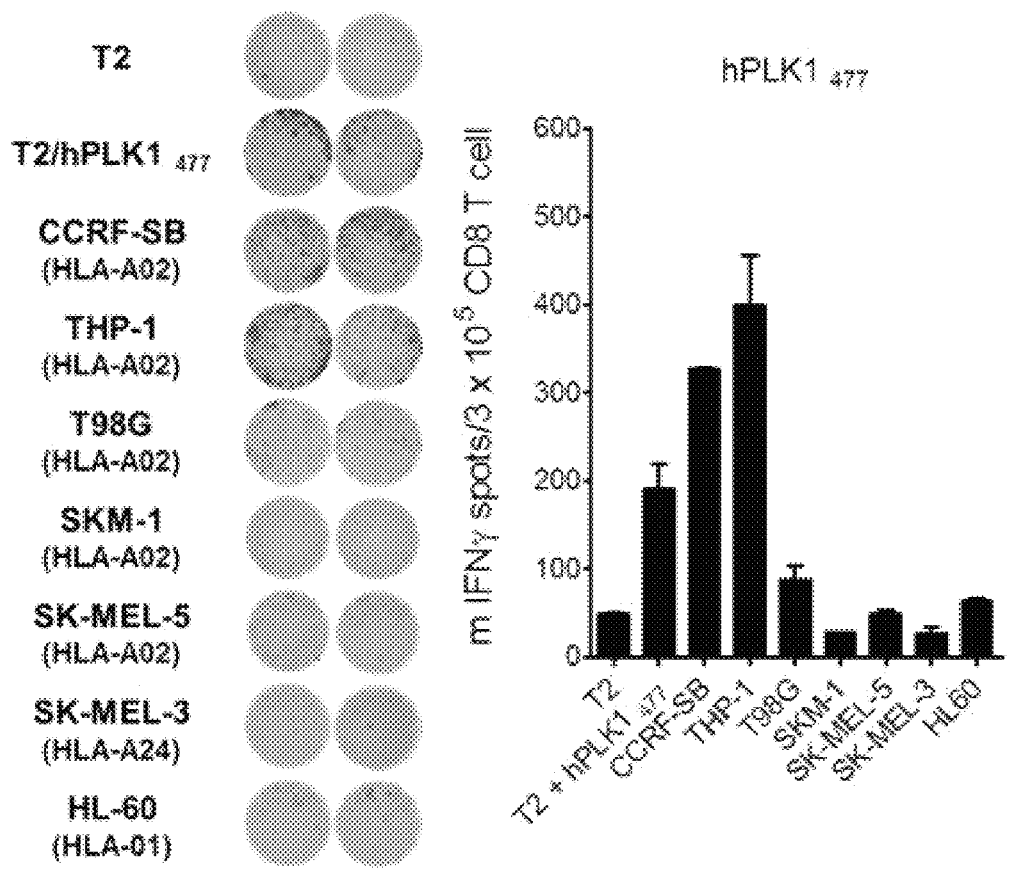
Figure 4C:
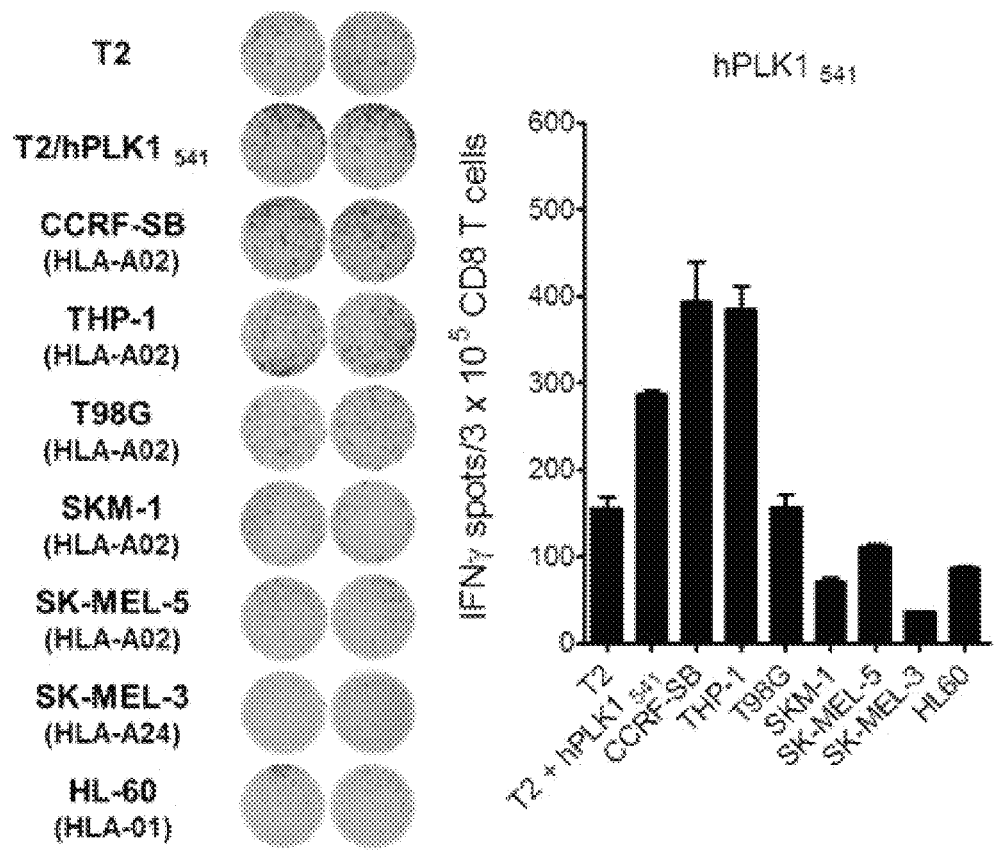

As illustrated in FIG. 4A to 4C, in not only an experimental group using $PLK1_{123}$ antigen peptides but all experimental groups using antigen-peptides, CD8+T cell responses specific for T2 cell lines and HLA-A2 positive tumor cells sensitized with PLK1-derived antigen-peptides were observed.

The present invention can be used for prevention or treatment of cancer.

---

SEQUENCE LISTING

```
<160> NUMBER OF SEQ ID NOS: 6

<210> SEQ ID NO 1
<211> LENGTH: 10
<212> TYPE: PRT
<213> ORGANISM: Artificial Sequence
<220> FEATURE:
<223> OTHER INFORMATION: Human Polo-like kinase-1

<400> SEQUENCE: 1

Ser Asp Phe Val Phe Val Val Leu Glu Leu
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Human Polo-like kinase-1

<400> SEQUENCE: 2

Thr Leu Leu Lys Tyr Phe Arg Asn Tyr Met
1               5                   10

<210> SEQ ID NO 3
<211> LENGTH: 10
<212> TYPE: PRT
<213> ORGANISM: Artificial Sequence
<220> FEATURE:
```

<223> OTHER INFORMATION: Human Polo-like kinase-1

<400> SEQUENCE: 3

Leu Ile Leu Cys Pro Leu Met Ala Ala Val
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Human Polo-like kinase-1

<400> SEQUENCE: 4

Ile Leu Cys Pro Leu Met Ala Ala Val
1               5

<210> SEQ ID NO 5
<211> LENGTH: 292
<212> TYPE: PRT
<213> ORGANISM: Artificial Sequence
<220> FEATURE:
<223> OTHER INFORMATION: Wild-types epitopes (PLKWT)

<400> SEQUENCE: 5

Met Ala Ala Ile Ile Leu His Leu Ser Asn Gly Ser Val Gly Ser
1               5                   10                  15

Gly Ile Leu Tyr Asn Asp Gly Asp Ser Leu Ser Gly Ser Gly Ser Leu
                20                  25                  30

Met Lys Lys Ile Thr Leu Leu Ser Gly Ser Gly Tyr Met Ser Glu His
            35                  40                  45

Leu Leu Lys Ala Ser Gly Ser Gly Ile Leu Cys Pro Leu Met Ala Ala
        50                  55                  60

Val Ser Gly Ser Gly Ser Asp Phe Val Phe Val Leu Glu Leu Ser
65                  70                  75                  80

Gly Ser Gly Asn Leu Phe Leu Asn Glu Asp Leu Glu Val Ser Gly Ser
                85                  90                  95

Gly Lys Leu Ile Leu Cys Pro Leu Met Ala Ala Ser Gly Ser Gly Leu
            100                 105                 110

Ile Leu Cys Pro Leu Met Ala Ala Val Ser Gly Ser Gly His Leu Ser
        115                 120                 125

Asp Met Leu Gln Gln Leu Ser Gly Ser Gly Val Leu Phe Asn Asp Ser
    130                 135                 140

Thr Arg Leu Ser Gly Ser Gly Phe Leu Asn Glu Asp Leu Glu Val Lys
145                 150                 155                 160

Ile Ser Gly Ser Gly Pro Leu Met Ala Ala Val Thr Tyr Ile Ser Gly
                165                 170                 175

Ser Gly Val Leu Phe Asn Asp Ser Thr Arg Leu Ile Ser Gly Ser Gly
                180                 185                 190

Lys Leu Ile Leu Cys Pro Leu Met Ala Ser Gly Ser Gly Thr Leu Leu
            195                 200                 205

Lys Tyr Phe Arg Asn Tyr Met Ser Gly Ser Gly Gln Leu Cys Asp Asn
        210                 215                 220

Ser Val Gly Val Ser Gly Ser Gly Lys Met Leu Gln Thr Asp Pro Thr
225                 230                 235                 240

Ala Ser Gly Ser Gly Ser Ile Gly Cys Ile Met Tyr Thr Leu Ser Gly
                245                 250                 255

Ser Gly Thr Pro Pro Ala Tyr Arg Pro Pro Asn Ala Pro Ile Leu Ser

```
                            260                 265                 270
Gly Ser Gly Gly Val Met Tyr Ala Phe Thr Thr Pro Leu Ile Ser Phe
            275                 280                 285

Phe Ala Ala Ala
    290

<210> SEQ ID NO 6
<211> LENGTH: 292
<212> TYPE: PRT
<213> ORGANISM: Artificial Sequence
<220> FEATURE:
<223> OTHER INFORMATION: Optimized epitopes (PLKOPT)

<400> SEQUENCE: 6

Met Ala Ala Ile Ile Leu His Leu Ser Asn Gly Ser Val Ser Gly Ser
1               5                   10                  15

Gly Ile Leu Tyr Asn Asp Gly Asp Ser Leu Ser Gly Ser Gly Ser Leu
            20                  25                  30

Met Lys Lys Ile Thr Leu Leu Ser Gly Ser Gly Tyr Met Ser Glu His
        35                  40                  45

Leu Leu Lys Val Ser Gly Ser Gly Ile Leu Cys Pro Leu Met Ala Ala
    50                  55                  60

Val Ser Gly Ser Gly Ser Asp Phe Val Phe Val Leu Glu Leu Ser
65                  70                  75                  80

Gly Ser Gly Asn Leu Phe Leu Asn Glu Asp Leu Glu Val Ser Gly Ser
                85                  90                  95

Gly Lys Leu Ile Leu Cys Pro Leu Met Ala Val Ser Gly Ser Gly Leu
            100                 105                 110

Met Leu Cys Pro Leu Met Ala Ala Val Ser Gly Ser Gly His Leu Ser
            115                 120                 125

Asp Met Leu Gln Gln Leu Ser Gly Ser Gly Val Leu Phe Asn Asp Ser
        130                 135                 140

Thr Arg Leu Ser Gly Ser Gly Phe Leu Asn Glu Asp Leu Glu Val Lys
145                 150                 155                 160

Val Ser Gly Ser Gly Pro Leu Met Ala Ala Val Thr Tyr Val Ser Gly
                165                 170                 175

Ser Gly Val Leu Phe Asn Asp Ser Thr Arg Leu Val Ser Gly Ser Gly
            180                 185                 190

Lys Leu Ile Leu Cys Pro Leu Met Val Ser Gly Ser Gly Thr Leu Leu
        195                 200                 205

Lys Tyr Phe Arg Asn Tyr Met Ser Gly Ser Gly Gln Leu Cys Asp Asn
    210                 215                 220

Ser Val Gly Val Ser Gly Ser Gly Lys Met Leu Gln Thr Asp Pro Thr
225                 230                 235                 240

Val Ser Gly Ser Gly Ser Leu Gly Cys Ile Met Tyr Thr Le

What is claimed is:

1. A peptide consisting of SEQ ID NO: 1, wherein the peptide is specific for Human Leukocyte Antigen A*02:01 (HLA-A*02:01).

2. An antigen presenting cell in which a complex comprising the peptide of claim 1 and an HLA-A*02:01 antigen is presented on its surface,
   wherein the antigen presenting cell is prepared b introducing a nucleic acid encoding the peptide of claim 1 into any one of a dendritic cell, a mononuclear cell, a CD4+T cell, a B cell, and a gamma delta T (γδ T) cell.

3. The antigen presenting cell of claim 2, wherein the nucleic acid is DNA or RNA.

4. A pharmaceutically-acceptable composition for stimulating an antigen-specific T cell response in an HLA-A2 positive human patient having a PLK1-expressing cancer, the composition comprising the antigen presenting cell of claim 2.

5. A method for stimulating an antigen-specific T cell response in an HLA-A2 positive human patient having a PLK1 expressing cancer, the method comprising: administering a pharmaceutically-effective amount of the pharmaceutically-acceptable composition of claim 4 to the HLA-A2 positive human patient having the PLK1-expressing cancer.

6. The pharmaceutically-acceptable composition according to claim 4, wherein the PLK1-expressing cancer is selected from the group consisting of colon cancer, gastric cancer, lung cancer, renal cell (RC) cancer, transitional cell (TC) cancer, prostate cancer, pancreatic cancer, breast cancer, ovary cancer, thyroid cancer, lymphoma, leukemia, and multiple myeloma (MM).

7. The method according to claim 5, wherein the PLK1-expressing cancer is from a cancer selected from the group consisting of colon cancer, gastric cancer, lung cancer, renal cell (RC) cancer, transitional cell (TC) cancer, prostate cancer, pancreatic cancer, breast cancer, ovary cancer, thyroid cancer, lymphoma, leukemia, and multiple myeloma (MM).

* * * * *